United States Patent
Daemmgen et al.

(10) Patent No.: US 8,883,123 B2
(45) Date of Patent: Nov. 11, 2014

(54) USE OF VACCINES FOR THE TREATMENT/PREVENTION OF THE TRANSMISSION OF PATHOGENS

(75) Inventors: Juergen Daemmgen, Ochsenhausen (DE); Eric Martin Vaughn, Ames, IA (US)

(73) Assignee: Boehringer Ingleheim Vetmedica, Inc., St. Joseph, MO (US)

( * ) Notice: Subject to any disclaimer, the term of this patent is extended or adjusted under 35 U.S.C. 154(b) by 0 days.

(21) Appl. No.: 11/553,492

(22) Filed: Oct. 27, 2006

(65) Prior Publication Data
US 2007/0207168 A1 Sep. 6, 2007

Related U.S. Application Data

(60) Provisional application No. 60/730,998, filed on Oct. 28, 2005.

(51) Int. Cl.
| | | |
|---|---|---|
| *A61K 49/00* | (2006.01) | |
| *A61K 39/12* | (2006.01) | |
| *A61K 39/145* | (2006.01) | |
| *C07K 1/00* | (2006.01) | |
| *C07K 14/005* | (2006.01) | |
| *A61K 39/00* | (2006.01) | |

(52) U.S. Cl.
CPC ..... *C07K 14/005* (2013.01); *A61K 2039/55511* (2013.01); *C12N 2760/16134* (2013.01); *A61K 2039/55* (2013.01); *A61K 2039/55566* (2013.01); *A61K 2039/525* (2013.01); *A61K 2039/552* (2013.01); *C12N 2760/16122* (2013.01); *A61K 39/145* (2013.01); *C12N 2710/14143* (2013.01)
USPC ... 424/9.2; 424/186.1; 424/204.1; 424/209.1; 530/396

(58) Field of Classification Search
CPC . A61K 39/145; A61K 2300/00; A61K 39/12; A61K 2039/70; A61K 2039/6075; A61K 47/4833; C12N 2760/16134; C12N 2760/16122; C12N 2760/16123; C12N 2760/16111; C12N 2760/16151; C12N 2760/16234; C12N 2760/16022; C12N 2710/14043; C12N 2710/24143; C12N 2760/16161; C12N 2760/16171; C12N 2760/16222; C12N 2760/16223; C12N 2760/16011; C12N 2760/16034; C12N 2760/16121; C12N 2760/16133; C12N 2760/16143; C07K 14/005; G01N 33/56983; G01N 2333/11
See application file for complete search history.

(56) References Cited

U.S. PATENT DOCUMENTS

| | | |
|---|---|---|
| 4,552,758 A | 11/1985 | Murphy et al. |
| 6,204,281 B1 | 3/2001 | Webb et al. |
| 8,202,967 B2 | 6/2012 | Vaughn et al. |
| 2004/0071733 A1 | 4/2004 | Takaku et al. |
| 2004/0219208 A1 | 11/2004 | Kawamura et al. |
| 2005/0042229 A1 | 2/2005 | Yang et al. |
| 2007/0207168 A1 | 9/2007 | Daemmgen et al. |
| 2012/0231027 A1 | 9/2012 | Vaughn et al. |
| 2014/0050755 A1 | 2/2014 | Vaughn et al. |

FOREIGN PATENT DOCUMENTS

| | | |
|---|---|---|
| CN | 1748795 A | 3/2006 |
| WO | WO2005107797 | 11/2005 |
| WO | 2006113214 A2 | 10/2006 |
| WO | 2007019094 A2 | 2/2007 |
| WO | 2007053446 A2 | 5/2007 |
| WO | 2008052173 A2 | 5/2008 |

OTHER PUBLICATIONS

Cinatl et al., The threat of avian influenza A (H5N1). Part IV: development of vaccines, 2007, Medical Microbiology and Immunology, vol. 196, pp. 213-225.*
Lim et al., Mucosal vaccination against influenza: Protection of pigs immunized with inactivated virus and ether-split vaccine, 2001, Japanese Journal of Veterinary Research, vol. 48, No. 4, pp. 197-203.*
Crawford et al., Baculovirus-derived hemagglutinin vaccines protect against lethal infuenza infections by avian H5 and H7 subtypes, 1999, Vaccine, vol. 17, pp. 2265-2274.*
Hien et al., Avian Influenza—A Challenge to Global Health Care Structures, 2004, New England Journal of Medicine, vol. 351, No. 23, pp. 2363-2365.*
Karasin et al., Isolation and Characterization of H4N6 Avian Influenza Viruses from Pigs with Pneumonia in Canada, 2000, Journal of Virology, vol. 74, No. 19, pp. 9322-9327.*
Claas, et al., "Human influenza A H5N1 virus related to a highly pathogenic avian influenza virus". Feb. 1998, The Lancet, vol. 351, No. 9101, pp. 471-477.
Genbank: AAT39065, Version AAT39065.1 GI:47834860, Jun. 6, 2004.
Genbank: AAT39066, Version AAT39066.1 GI:47834862, Jun. 6, 2004.
Genbank: ABA55715, Version ABA55715.1 GI:76800616, Oct. 8, 2005.
Genbank: AY575870, Version AY575870.1 GI:47834861, Jun. 6, 2004.

(Continued)

*Primary Examiner* — Benjamin P Blumel
(74) *Attorney, Agent, or Firm* — Michael P. Morris; Wendy M. Gombert

(57) ABSTRACT

The present invention relates to a method of reducing the transmission of a pathogen from an animal of a first species to an animal of a second species. Specifically, reduction of transmission is accomplished through the administration of antigen of the pathogen such that administration results in the reduction or absence of the reproduction of the pathogen in the animal to which the antigen was administered.

5 Claims, 2 Drawing Sheets

(56) References Cited

OTHER PUBLICATIONS

Guan et al., "H5N1 influenza: A protean pandemic threat". Proceedings of the National Acadmey of Sciences, vol. 101, No. 21, May 2004, pp. 8156-8161.
Hoffmann et al., "Role of specific hemagglutinin amino acids in the immunogenicity and protection of H5N1 influenza virus vaccines". Sep. 2005, Proceedings of the National Academy of Sciences, vol. 102, No. 36, pp. 12915-12920.
Iino et al., "Renoprotective Effect of Losartan in Comparison to Amlodipine in Patients with Chronic Kidney Disease and Hypertension—a Report of the Japanese Losartan Therapy Intended for the Global Renal Protection in Hypertensive Patients (JLIGHT) Study." 2004, Hypertension Research, vol. 27, No. 1, pp. 21-30.
Ioannou, et al., "The Immunogenicity and Protective Efficacy of Bovine Herpesvirus 1 Glycoprotein D plus Emulsigen Are Increased by Formulation with CpG Oligodeoxynucleotides". Sep. 2002, Journal of Virology, vol. 76, No. 18, pp. 9002-9010.
Knossow et al., "Variation and infectivity neutralization in influenza". 2006, Immunology, vol. 119, pp. 1-7.
Lefebvre et al., "Angiotensin-converting enzyme inhibitors in the therapy of renal diseases". 2004, Journal of Veterinary Pharmacology and Therapeutics, vol. 27, No. 5, pp. 265-281.
Lipatov et al., "Influenza: Emergence and Control". Sep. 2004, Journal of Virology, vol. 78, No. 17, pp. 8951-8959.
Nwe et al., "Expression of hemagglutinin protein from the avian influenza virus H5N1 in a baculovirus/insect cell system significantly enhanced by suspension culture". BMC Microbiology, vol. 6, No. 16, 2006, (http://www.biomedcentral.com/1471-2180/6/16).
Philpott, et al., "Hemagglutinin Mutations Related to Attenuation and Altered Cell Tropism of a Virulent Avian Influenza A Virus". Jun. 1990, Journal of Virology, vol. 64, No. 6, pp. 2941-2947.
Senne, et al., "Survey of the Hemagglutinin (HA) Cleavage Site Sequence of H5 and H7 Avian Influenza Viruses: Amino Acid Sequence at the HA Cleavage Site as a Marker of Pathogenicity Potential". 1996, Avian Diseases, vol. 40, No. 2, pp. 425-437.
Snively et al., "Chronic Kidney Disease: Prevention and Treatment of Common Complications". Nov. 2004, American Family Physician, vol. 70, No. 10, pp. 1921-1928.
Stevens, et al., "Structure and Receptor Specificity of the Hemagglutinin from an H5N1 Influenza Virus". Apr. 2006, Science, vol. 312, pp. 404-410.
Subbarao et al., "Avian influenza viruses infecting humans". 2000, Cellular and Molecular Life Sciences, vol. 57, pp. 1770-1784.
Suga et al., "Angiotensin II type 1 receptor blockade ameliorates tubulointerstitial injury induced by chronic potassium deficiency". 2002, Kidney International, vol. 61, pp. 951-958.
Viseshakul et al., "The genome sequence analysis of H5N1 avian influenza A virus isolated from the outbreak among poultry populations in Thailand". Virology, vol. 328, 2003, pp. 169-176.
White et al., "Effects of the Angiotensin II Receptor Blockers Telmisartan Versus Valsartan on the Circadian Variation of Blood Pressure. Impact on the Early Morning Period". 2004, American Journal of Hypertension, vol. 17, pp. 347-353.
WHO Global Influenza Program Surveillance Network, "Evolution of H5N1 Avian Influenza Viruses in Asia," Emerging Infectious Diseases, vol. 11, No. 20, 2005 pp. 1515-1521.
Written Opinion of the International Searching Authority for PCT/US2006/041989 mailed on Jun. 29, 2007.
Liu, et al: "Sequence comparison between the extracellular domain of M2 protein human an avian influenza A virus provides new information for bivalent influenza vaccine design" 2005,p. 171-177, vol. 7, No. 2, Microbes and Infection, Elsevier, Paris, France.
Pushko, et al: "Influenza virus-like particles comprised of the HA, NA, and MI proteins of H9N2 influenza virus induce protective immune responses in BALB/c mice"2005, p. 5751-5759,vol. 23,No. 50, Vaccine, Butterworth Scientific, Guildford, Great Britain.
Stephenson, et al: "Cross-Reactivity to highly Pathogenic Avian Influenza H5N1 Viruses after Vaccination with Nonadjuvanted and MF59-Adjuvanted Influenza A/Duck/Singapore/97 (H5N3) vaccine: A Potential Priming Strategy" Influenza Branch, Centers for Disease Control and Prevention, Georgia, USA. Chiron Vaccines, Siena, Italy, Infectious Diseases Unit, Leicester Royal Infirmary, Leicester and National Institute for Biological Standards and Control, Potters Bar and Central Public Health Laboratory, Health Protection Agency, Colindale, UK, 2005.
Luschow, et al: "Protection of chickens from lethal avian influenza A virus infection by live-virus vaccination with infectious laryngotracheitis virus recombinants expressing" 2001, p. 4249-4259, vol. 19, No. 30, Vaccine, Butterworth Scientific. Guildford, GB, Institute of Molecular Biology, Freedrich-Loeffler-Institutes, Federal research Centre for Virus Diseases of Animals, Institute of Diagonostic Virolgy, Fried-Loeffler-Institutes, Federal Research for Virus Diseases of Animals, Insel Riems, Germany.
Philippa, et al: "Highly pathogenic avian influenza (H7N7): Vaccination of zoo birds and transmission to non-poultry species" 2005, p. 5743-5750, vol. 23, No. 50, Vaccine, Butterworth scientific, Guildford, GB,Institute of Virology,. Dutch Wildlife Health Centre, and Utrecht University, Utrecht, The Netherlands.
Palese,et al: "Influenza: Old and new threats" 2004, p. 582-587,vol. 10, No. 12, Nature Medicine, Nature America, NY, USA.
Stephenson, et al: "Conforming the avian influenza threat: vaccine development for potential pandemic" 2004, vol. 4, The Lancet Infectious Diseases.
Thomson, "Vaccine Leader: Swine influenza virus . . . combination of pathogenic avian influenza and human influenza" 2006, XP002437726, Database accession No. 2007-182327.
International Search Report, PCT/US2006/041989 Jul. 15, 2007.

* cited by examiner

```
                                                                  36
HK/213/03                XXXXXXXHANNWTEQVDTIMEKNVTVTHAQDILEKTHN 38
BIV H5 HA    GSATMEKTVLLLAIVSLVKSDQICIGYHANNSTEQVDTIMEKNVTVTHAQDILEKTHN 58

83    86
HK/213/03    GKLCDLDGVKPLILRDCSVAGWLLGNPMCDEFINVPEWSYIVEKANPANDLCYPGDFN 96
BIV H5 HA    GKLCDLDGVKPLILRDCSVAGWLLGNPMCDEFINVPEWSYIVEKANPANDLCYPGNFN 116

120
HK/213/03    DYEELKHLLSRINHFEKIQIIPKNSWSSHEASLGVSSACPYQGKSSFFRNVVWLIKKN 154
BIV H5 HA    DYEELKHLLSRINHFEKIQIIPKSSWSDHEASSGVSSACPYQGSSSFFRNVVWLIKKN 174

155156                          189               212
HK/213/03    NAYPTIKRSYNNTNQEDLLVLWGIHHPNDAAEQTRLYQNPTTYISVGTSTLNQRLVPK 212
BIV H5 HA    DAYPTIKRSYNNTNQEDLLVLWGIHHPNDAAEQTRLYQNPTTYISVGTSTLNQRLVPK 232

223                               263
HK/213/03    IATRSKVNGQNGRMEFFWTILKPNDAINFESNGNFIAPEYAYKIVKKGDSAIMKSELE 270
BIV H5 HA    IATRSKVNGQSGRMDFFWTILKPNDAINFESNGNFIAPEYAYKIVKKGDSAIMKSEVE 290
```

HK/213/03:   Translation A/HK/213/03 (H5N1) hemagglutinin (HA) gene, partial cds.

BIV H5 HA:   Translation of BIV G00692 H5 HA derived from A/duck/China/E319-2/03(H5N1)

HK/213/03 = Seq. ID No. 7

BIV H5 HA = Seq. ID No. 6

```
                           SEQUENCE LISTING

<160> NUMBER OF SEQ ID NOS: 7

<210> SEQ ID NO 1
<211> LENGTH: 551
<212> TYPE: PRT
<213> ORGANISM: Avian influenza virus

<400> SEQUENCE: 1

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Gln Gly Ser Ser Ser Phe Phe
    130                 135                 140

Arg Asn Val Val Trp Leu Ile Lys Lys Asn Asp Ala Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Val Gly Thr Ser Thr Leu Asn Gln Arg
        195                 200                 205

Leu Val Pro Lys Ile Ala Thr Arg Ser Lys Val Asn Gly Gln Ser Gly
    210                 215                 220

Arg Met Asp Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Val Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Lys Leu Val Leu Ala Thr Gly Leu Arg Asn Ser
305                 310                 315                 320

Pro Gln Arg Glu Arg Arg Arg Lys Arg Gly Leu Phe Gly Ala Ile Ala
                325                 330                 335

Gly Phe Ile Glu Gly Gly Trp Gln Gly Met Val Asp Gly Trp Tyr Gly
```

```
            340                 345                 350
Tyr His His Ser Asn Glu Gln Gly Ser Gly Tyr Ala Ala Asp Lys Glu
                355                 360                 365

Ser Thr Gln Lys Ala Ile Asp Gly Val Thr Asn Lys Val Asn Ser Ile
    370                 375                 380

Ile Asp Lys Met Asn Thr Gln Phe Glu Ala Val Gly Arg Glu Phe Asn
385                 390                 395                 400

Asn Leu Glu Arg Arg Ile Glu Asn Leu Asn Lys Lys Met Glu Asp Gly
                405                 410                 415

Phe Leu Asp Val Trp Thr Tyr Asn Ala Glu Leu Leu Val Leu Met Glu
            420                 425                 430

Asn Glu Arg Thr Leu Asp Phe His Asp Ser Asn Val Lys Asn Leu Tyr
                435                 440                 445

Asp Lys Val Arg Leu Gln Leu Arg Asp Asn Ala Lys Glu Leu Gly Asn
    450                 455                 460

Gly Cys Phe Glu Phe Tyr His Lys Cys Asp Asn Glu Cys Met Glu Ser
465                 470                 475                 480

Val Arg Asn Gly Thr Tyr Asp Tyr Pro Gln Tyr Ser Glu Glu Ala Arg
                485                 490                 495

Leu Lys Arg Glu Glu Ile Ser Gly Val Lys Leu Glu Ser Ile Gly Thr
            500                 505                 510

Tyr Gln Ile Leu Ser Ile Tyr Ser Thr Val Ala Ser Ser Leu Ala Leu
                515                 520                 525

Ala Ile Met Val Ala Gly Leu Ser Leu Trp Met Cys Ser Asn Gly Ser
    530                 535                 540

Leu Gln Cys Arg Ile Cys Ile
545                 550

<210> SEQ ID NO 2
<211> LENGTH: 567
<212> TYPE: PRT
<213> ORGANISM: duck influenza virus

<400> SEQUENCE: 2

Met Glu Lys Thr Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Ser Ser Ser Phe Phe
145                 150                 155                 160
```

```
Arg Asn Val Val Trp Leu Ile Lys Lys Asn Asp Ala Tyr Pro Thr Ile
            165                 170                 175
Lys Arg Ser Tyr Asn Asn Thr Asn Gln Glu Asp Leu Leu Val Leu Trp
        180                 185                 190
Gly Ile His His Pro Asn Asp Ala Ala Glu Gln Thr Arg Leu Tyr Gln
        195                 200                 205
Asn Pro Thr Thr Tyr Ile Ser Val Gly Thr Ser Thr Leu Asn Gln Arg
    210                 215                 220
Leu Val Pro Lys Ile Ala Thr Arg Ser Lys Val Asn Gly Gln Ser Gly
225                 230                 235                 240
Arg Met Asp Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
            260                 265                 270
Val Lys Lys Gly Asp Ser Ala Ile Met Lys Ser Glu Val Glu Tyr Gly
        275                 280                 285
Asn Cys Asn Thr Lys Cys Gln Thr Pro Met Gly Ala Ile Asn Ser Ser
    290                 295                 300
Met Pro Phe His Asn Ile His Pro Leu Thr Ile Gly Glu Cys Pro Lys
305                 310                 315                 320
Tyr Val Lys Ser Asn Lys Leu Val Leu Ala Thr Gly Leu Arg Asn Ser
                325                 330                 335
Pro Gln Arg Glu Arg Arg Arg Lys Arg Gly Leu Phe Gly Ala Ile Ala
            340                 345                 350
Gly Phe Ile Glu Gly Gly Trp Gln Gly Met Val Asp Gly Trp Tyr Gly
        355                 360                 365
Tyr His His Ser Asn Glu Gln Gly Ser Gly Tyr Ala Ala Asp Lys Glu
    370                 375                 380
Ser Thr Gln Lys Ala Ile Asp Gly Val Thr Asn Lys Val Asn Ser Ile
385                 390                 395                 400
Ile Asp Lys Met Asn Thr Gln Phe Glu Ala Val Gly Arg Glu Phe Asn
                405                 410                 415
Asn Leu Glu Arg Arg Ile Glu Asn Leu Asn Lys Lys Met Glu Asp Gly
            420                 425                 430
Phe Leu Asp Val Trp Thr Tyr Asn Ala Glu Leu Leu Val Leu Met Glu
        435                 440                 445
Asn Glu Arg Thr Leu Asp Phe His Asp Ser Asn Val Lys Asn Leu Tyr
    450                 455                 460
Asp Lys Val Arg Leu Gln Leu Arg Asp Asn Ala Lys Glu Leu Gly Asn
465                 470                 475                 480
Gly Cys Phe Glu Phe Tyr His Lys Cys Asp Asn Glu Cys Met Glu Ser
                485                 490                 495
Val Arg Asn Gly Thr Tyr Asp Tyr Pro Gln Tyr Ser Glu Glu Ala Arg
            500                 505                 510
Leu Lys Arg Glu Glu Ile Ser Gly Val Lys Leu Glu Ser Ile Gly Thr
        515                 520                 525
Tyr Gln Ile Leu Ser Ile Tyr Ser Thr Val Ala Ser Ser Leu Ala Leu
    530                 535                 540
Ala Ile Met Val Ala Gly Leu Ser Leu Trp Met Cys Ser Asn Gly Ser
545                 550                 555                 560
Leu Gln Cys Arg Ile Cys Ile
                565
```

<210> SEQ ID NO 3
<211> LENGTH: 568
<212> TYPE: PRT
<213> ORGANISM: duck influenza virus

<400> SEQUENCE: 3

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Asn Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Asn Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380
```

```
Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
        530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 4
<211> LENGTH: 568
<212> TYPE: PRT
<213> ORGANISM: Avian influenza virus

<400> SEQUENCE: 4

Met Glu Lys Thr Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Asn Ser Trp Ser Asp His Glu Ala Ser
    130                 135                 140

Ser Gly Val Ser Ser Ala Cys Pro Tyr Gln Gly Ser Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190
```

```
Gly Ile His His Pro Asn Asp Ala Ala Glu Gln Thr Arg Leu Tyr Gln
            195                 200                 205

Asn Pro Thr Thr Tyr Ile Ser Val Gly Thr Ser Thr Leu Asn Gln Arg
        210                 215                 220

Leu Val Pro Lys Ile Ala Thr Arg Ser Lys Val Asn Gly Gln Asn Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Ala Ile Met Lys Ser Glu Val Glu Tyr Gly
            275                 280                 285

Asn Cys Asn Thr Lys Cys Gln Thr Pro Met Gly Ala Ile Asn Ser Ser
        290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Gln Arg Glu Arg Arg Lys Lys Arg Gly Leu Phe Gly Ala Ile
                340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
        450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
            515                 520                 525

Thr Tyr Gln Ile Leu Ser Ile Tyr Ser Thr Val Ala Ser Ser Leu Ala
        530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 5
<211> LENGTH: 263
<212> TYPE: PRT
<213> ORGANISM: Avian influenza virus
```

```
<400> SEQUENCE: 5

His Ala Asn Asn Trp Thr Glu Gln Val Asp Thr Ile Met Glu Lys Asn
1               5                   10                  15

Val Thr Val Thr His Ala Gln Asp Ile Leu Glu Lys Thr His Asn Gly
            20                  25                  30

Lys Leu Cys Asp Leu Asp Gly Val Lys Pro Leu Ile Leu Arg Asp Cys
        35                  40                  45

Ser Val Ala Gly Trp Leu Leu Gly Asn Pro Met Cys Asp Glu Phe Ile
    50                  55                  60

Asn Val Pro Glu Trp Ser Tyr Ile Val Glu Lys Ala Asn Pro Ala Asn
65                  70                  75                  80

Asp Leu Cys Tyr Pro Gly Asp Phe Asn Asp Tyr Glu Glu Leu Lys His
                85                  90                  95

Leu Leu Ser Arg Ile Asn His Phe Glu Lys Ile Gln Ile Ile Pro Lys
            100                 105                 110

Asn Ser Trp Ser Ser His Glu Ala Ser Leu Gly Val Ser Ser Ala Cys
        115                 120                 125

Pro Tyr Gln Gly Lys Ser Ser Phe Phe Arg Asn Val Val Trp Leu Ile
    130                 135                 140

Lys Lys Asn Asn Ala Tyr Pro Thr Ile Lys Arg Ser Tyr Asn Asn Thr
145                 150                 155                 160

Asn Gln Glu Asp Leu Leu Val Leu Trp Gly Ile His His Pro Asn Asp
                165                 170                 175

Ala Ala Glu Gln Thr Arg Leu Tyr Gln Asn Pro Thr Thr Tyr Ile Ser
            180                 185                 190

Val Gly Thr Ser Thr Leu Asn Gln Arg Leu Val Pro Lys Ile Ala Thr
        195                 200                 205

Arg Ser Lys Val Asn Gly Gln Asn Gly Arg Met Glu Phe Phe Trp Thr
    210                 215                 220

Ile Leu Lys Pro Asn Asp Ala Ile Asn Phe Glu Ser Asn Gly Asn Phe
225                 230                 235                 240

Ile Ala Pro Glu Tyr Ala Tyr Lys Ile Val Lys Lys Gly Asp Ser Ala
                245                 250                 255

Ile Met Lys Ser Glu Leu Glu
            260

<210> SEQ ID NO 6
<211> LENGTH: 290
<212> TYPE: PRT
<213> ORGANISM: duck influenza virus

<400> SEQUENCE: 6

Gly Ser Ala Thr Met Glu Lys Thr Val Leu Leu Leu Ala Ile Val Ser
1               5                   10                  15

Leu Val Lys Ser Asp Gln Ile Cys Ile Gly Tyr His Ala Asn Asn Ser
            20                  25                  30

Thr Glu Gln Val Asp Thr Ile Met Glu Lys Asn Val Thr Val Thr His
        35                  40                  45

Ala Gln Asp Ile Leu Glu Lys Thr His Asn Gly Lys Leu Cys Asp Leu
    50                  55                  60

Asp Gly Val Lys Pro Leu Ile Leu Arg Asp Cys Ser Val Ala Gly Trp
65                  70                  75                  80

Leu Leu Gly Asn Pro Met Cys Asp Glu Phe Ile Asn Val Pro Glu Trp
                85                  90                  95
```

```
Ser Tyr Ile Val Glu Lys Ala Asn Pro Ala Asn Asp Leu Cys Tyr Pro
            100                 105                 110

Gly Asn Phe Asn Asp Tyr Glu Glu Leu Lys His Leu Leu Ser Arg Ile
        115                 120                 125

Asn His Phe Glu Lys Ile Gln Ile Ile Pro Lys Ser Ser Trp Ser Asp
    130                 135                 140

His Glu Ala Ser Ser Gly Val Ser Ser Ala Cys Pro Tyr Gln Gly Ser
145                 150                 155                 160

Ser Ser Phe Phe Arg Asn Val Val Trp Leu Ile Lys Lys Asn Asp Ala
                165                 170                 175

Tyr Pro Thr Ile Lys Arg Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Arg Leu Tyr Gln Asn Pro Thr Thr Tyr Ile Ser Val Gly Thr Ser Thr
    210                 215                 220

Leu Asn Gln Arg Leu Val Pro Lys Ile Ala Thr Arg Ser Lys Val Asn
225                 230                 235                 240

Gly Gln Ser Gly Arg Met Asp Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270

Ala Tyr Lys Ile Val Lys Lys Gly Asp Ser Ala Ile Met Lys Ser Glu
        275                 280                 285

Val Glu
    290

<210> SEQ ID NO 7
<211> LENGTH: 270
<212> TYPE: PRT
<213> ORGANISM: Avian influenza virus
<220> FEATURE:
<221> NAME/KEY: MISC_FEATURE
<222> LOCATION: (1)..(7)
<223> OTHER INFORMATION: X can be any amino acid

<400> SEQUENCE: 7

Xaa Xaa Xaa Xaa Xaa Xaa Xaa His Ala Asn Asn Trp Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Ala Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Asn Ser Trp Ser Ser His Glu Ala Ser
        115                 120                 125

Leu Gly Val Ser Ser Ala Cys Pro Tyr Gln Gly Lys Ser Ser Phe Phe
    130                 135                 140

Arg Asn Val Val Trp Leu Ile Lys Lys Asn Asn Ala Tyr Pro Thr Ile
```

```
145                 150                 155                 160
Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Val Gly Thr Ser Thr Leu Asn Gln Arg
        195                 200                 205

Leu Val Pro Lys Ile Ala Thr Arg Ser Lys Val Asn Gly Gln Asn Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu
                260                 265                 270
```

USE OF VACCINES FOR THE TREATMENT/PREVENTION OF THE TRANSMISSION OF PATHOGENS

FIELD OF THE INVENTION

The present invention relates to the field of medicine, preferably to the field of infectious diseases. In particular the present invention relates to the vaccination of animals of a first species in order to prevent intra-species transmission ("horizontal transmission") as well as inter-species transmissions ("vertical transmission") of pathogens. More particularly, the present invention relates to influenza vaccines and their use for the treatment and prevention of influenza infections, furthermore for the prevention of intra- and inter-species transmission of influenza.

BACKGROUND IF THE INVENTION

Influenza infection remains an important infection in animals and humans. Influenza is caused by viruses that undergo continuous antigenic changes/modifications and that possess an animal reservoir. Thus new epidemics and pandemics may occur in the future, and eradication of the disease will be difficult to achieve. Influenza viruses are well known in the art and described more in detail for example by P. Palese, *Nature Medicine*, vol. 10, no. 12, pp. S 82 to S 86 of December 2004, with further references. Briefly, the genome of the influenza A virus consists of eight single-stranded segments, and the viral particles has two major glycoproteins on its surface: hemagglutinin (H) and neuraminidase (N). With at least 15 different hemagglutinin (H1 to H15) and 9 different neuraminidase (N1 to N9) subtypes, there is a considerable antigenic variation among influenza viruses.

Influenza virus of type H5N1 Fowl Plague virus has been demonstrated to infect both pigs and man. The viruses can also be transmitted directly from avian species to humans (Claas et al., *Lancet* 1998, 351: 472; Suarez et al., *J. Virol.* 1998, 72: 6678; Subbarao et al., *Science* 1998, 279: 393; Shortridge, *Vaccine* 1999, 17 (Suppl. 1): S26-S29). Mortality in known human clinical cases approaches about 50%.

Over the last century pigs have been an important vector for influenza pandemics. Pigs, camels, and seals, preferably pigs, can serve as a 'mixing chamber' for avian influenza viruses, and therefore represent a potential risk factor for overcoming the species hurdles from poultry, the naturally reservoir of influenza viruses, to mammals. This normally occurs by double infections of the susceptible animals, e.g. pig, with both, an established mammalian (porcine), as well as an avian influenza virus. This double infection may create new recombinant viruses that may be the cause of human or porcine pandemics. Recent evidence would, however, indicate that a recombination of current avian H5 strains with mammalian influenza viruses will not result in highly virulent recombinants. On the other hand, avian influenza virus can infect pigs and by spontaneous mutations can become adapted to pigs. The critical hurdle will be overcome as soon as the virus can cause horizontal infections within a pig (or other mammalian) population.

Yet, a major part of Southeast Asian pigs have been infected with avian (H5) influenza virus strains originating from neighbouring poultry husbandry. As those infections have so far been sub-clinical, they can only be diagnosed by laboratory methods and thus are frequently overlooked. There is a high risk that those sub-clinically-infected pigs will serve as an opportunity for the virus to adapt to the mammalian system, spread within the porcine population, and also infect human beings.

As the species hurdle between pigs and humans is expected to be low the risk of horizontal infections of the variant 'porcine' influenza viruses within humans is dramatically increased. The currently available vaccines against influenza A infection are killed-virus vaccine preparations, that contain variants of the H1, H2 and H3 subtype of influenza. The use of those vaccines is limited to the vaccination of humans in order to prevent transmission from man to man. Thus those vaccines, including the current vaccination strategy to prevent man-to-man transmission, are not preventive with respect to the transmission and adaptation of non-mammalian influenza viruses to mammalians. Those vaccines, including the current vaccination strategy does not sufficiently consider the fact that non-mammalian influenza viruses, e.g. avian influenza viruses are able to infect non-human mammals, such as pigs, camels, seals, etc, and to recombine with mammalian influenza viruses in those non-human mammals.

Thus, there is a need to increase availability of new superior vaccines and new vaccination approaches to provide better approaches to control influenza infections and to have a positive impact on disease load.

DESCRIPTION OF THE FIGURES

FIG. 2 shows the amino acid sequences of two H5 polypeptides.

DESCRIPTION OF THE INVENTION

Figure 1:
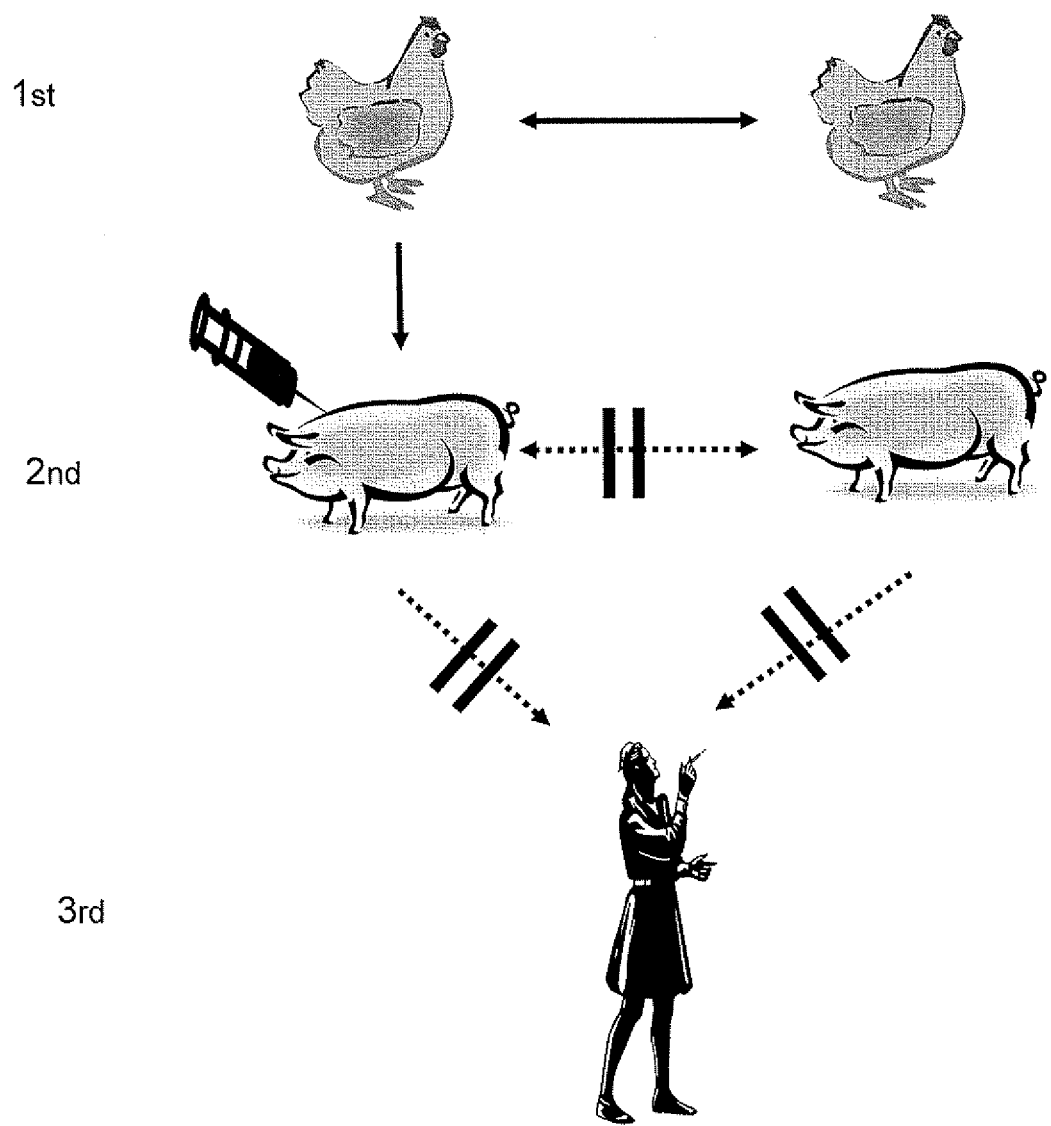
FIG. 1 shows the inventive idea provided herein. Immunization of animals of a second species (e.g. pig) against a pathogen (e.g. influenza H5N1) of an animal of a first species (poultry) prevents, or at least reduce the transmission of the pathogen of the first species to an other animal of the same species (e.g. pig to pig) or to a third species (e.g. pig to human).

It has been surprisingly found that pigs can be effective vaccinated against avian influenza virus (See Example 2, RESULTS). By vaccinating pigs with a suitable vaccine comprising an antigen of avian influenza virus, preferably H1, H3, H5, H7 and/or H9, more preferred H5 and/or H7, the risk of generating variant influenza strains adapted to pigs can be reduced or completely eliminated. As a result, the adaptation of an avian influenza virus on humans can be reduced or completely eliminated due to the elimination of the virus within a naturally mammalian reservoir of the influenza virus. Thus one aspect of the present invention pertains the generation of a vaccine, preferably a recombinant vaccine, based on avian influenza hemagglutinin of subtypes 1, 3, 5, 7 and/or 9 (i.e. H1, H3, H5, H7 and/or H9) for the vaccination of pigs in order to prevent or reduce reproduction of avian influenza viruses in pigs, when infected with an avian influenza virus comprising the same antigen or an antigen, that shows cross-reactivity with the antigen(s) used for vaccination.

The term "reproduction", as used herein, includes but is not limited to the replication of the viral genome and/or the particle assembly. The term "reduce" or "reduction of reproduction" as used herein means, that the replication rate in vaccinated animals is statistically significant lower than in non-vaccinated animals. In other words, the titers of avian influenza virus in pigs challenged with an infectious influenza virus is in the arithmetic average lower than in pigs that have not been vaccinated before the challenge. By the term "in the arithmetic average lower" is meant, a reduction of more than 20%, preferably more than 40%, even preferred more than 50%, even more preferred more than 80%, even more preferred more than 100%. In this connection, the term "eliminated" means, that no virus replication is detectable in vaccinated pips challenged with the infectious influenza virus after day 10, preferably after day 9, more preferably after day 8, even preferably after day 7, even more preferably after day 6, even more preferably after day 5, even more preferably after day 4, even more preferably after day 6, even more preferably after day 3, even more preferably after day 2, most preferred after day 1 of the challenge.

According to a more general aspect, the present invention relates to the use of an antigenic composition that comprises an antigen of a pathogen of an animal of a first species for the preparation of a pharmaceutical composition for the immunization of an animal of a second species, wherein said pharmaceutical composition, when administered to the animal of the second species, results in a reduction or the absence of the reproduction of a pathogen infectious to an animal of the first species, in an animal of the second species, when said animal of the second species is infected with said infectious pathogen of the animal of the first species, preferably provided that the antigen of the antigenic composition of the pharmaceutical composition is present in or on the infectious pathogen.

The first species and the second species can be of the same species or of different species. Preferably the first and second species are different, even more preferably the first species is a poultry, e.g. bird, chicken, duck, turkey etc., and the second species is a mammal, preferably a pig, cattle, horse, seals, camels, dog, cat, hamster, mouse, human, most preferred a pig.

Thus according to another aspect, the present invention relates to the use of an antigenic composition that comprises an antigen of a pathogen of poultry for the preparation of a pharmaceutical composition for the immunization of a mammal, wherein said pharmaceutical composition, when administered to the mammal results in a reduction or the absence of the reproduction of the pathogen infectious to poultry in an mammal, when said mammal is infected with said infectious pathogen of poultry, provided that the antigen of the antigenic composition of the pharmaceutical composition is present in or on the infectious pathogen.

The term "pharmaceutical composition" as described herein, includes but is not limited to vaccines for the reduction or prevention of an infection or to a composition of matter for the treatment and lessening of an infection.

The term "pathogen" as used includes but is not limited to a microorganism or any pathogenic part thereof, that normally causes diseases or illness to its host, or at least disrupt the normal physiology of its host. For example, an pathogen of poultry is the avian influenza virus.

Thus according to a further aspect of the present invention, the pathogen according to the invention being infectious to poultry is an influenza virus, preferably the avian influenza virus. According to a further aspect of the present invention, the pathogen being infectious to the poultry is an avian influenza virus of subtype H1, H3, H5, H7 or H9, more preferably an avian influenza virus of subtype H5 or H7, most preferably an avian influenza virus of subtype H5N1.

The term "antigenic composition" as used herein means a composition of matter that comprises one or more antigens.

The term "antigen" as used herein means but is not limited to peptides, polypeptides, glycopeptides, or polysaccharides which are capable of specifically interacting with an antigen recognition molecule of the immune system, such as an immunoglobulin (antibody) or T cell antigen receptor in order to elicit, activate or stimulate an immune response directed to said antigen in a host to which said antigen is administered. The term "antigen" also refers to nucleic acid molecules, preferably DNA- or RNA-molecules, each of which codes for and express a peptide, polypeptide, or glycopeptide that is capable of specifically interacting with an antigen recognition molecule of the immune system, such as an immunoglobulin (antibody) or T cell antigen receptor in order to elicit, activate or stimulate an immune response against the antigen that is encoded by the nucleic acid molecule. The antigen used for the preparation of the pharmaceutical composition which is used according to the invention is a microorganism or an antigenic part and/or preparation of said microorganism. In this connection, the term "immunization, as used herein, means but is not limited to any cause or enhancement of an immune response.

The term "immune response" as used means but is not limited to a cellular and/or antibody-mediated immune response to a composition or vaccine of interest. Usually, an "immune response" includes but is not limited to one or more of the following effects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of the symptoms associated with host infections as described above.

The term "antigenic part and/or preparation thereof" as used herein means that at least one molecule of said part and/or preparation is antigenic or possess antigenic properties. The antigenic part and/or preparation of a microorganism includes but is not limited to peptides, polypeptides, glycopeptides, and/or polysaccharides including any fragments thereof, that possess antigenic property.

A molecule is "antigenic" or possess "antigenic properties" when it is capable of specifically interacting with an antigen recognition molecule of the immune system, such as an immunoglobulin (antibody) or T cell antigen receptor. An antigenic polypeptide for example contains an epitope of at least about five, and preferably at least about 10 amino acids. An antigenic portion of a polypeptide, also called herein "epitope", can be that portion of the polypeptide that is immunodominant for antibody or T cell receptor recognition, or it can be a portion of a polypeptide used to generate an antibody to the molecule by conjugating the antigenic portion to a carrier polypeptide for immunization. A molecule that is antigenic needs not to be itself immunogenic, i.e., capable of eliciting an immune response without a carrier. In other words, an antigenic portion also includes but is not limited to a hapten which needs to be conjugated to a carrier in order to become immunogenic.

As mentioned above, the antigen can be a microorganism or an antigenic part and/or preparation thereof. Preferably, said the microorganism is a virus, or an antigenic part and/or preparation thereof, and most preferably an influenza virus, or an antigenic part and/or preparation thereof. According to a further aspect of the invention, the antigen used for the preparation of the pharmaceutical composition is an avian influenza virus, or an antigenic part and/or preparation thereof.

According to a further aspect of the invention, the antigen used for the preparation of the pharmaceutical composition is the hemagglutinin (H) and/or the neuraminidase (N) of influenza virus. Preferably, said antigen is H1, H3, H5, H7, and/or H9 of the avian influenza virus. In this context, the term "and/or" means, that single antigen or any combinations of the antigens mentioned above, can be used for the preparation of the pharmaceutical composition. In contrast to the H1 or H3 strains, currently present in the pig population, the H5 and probably H7 appears to be more conserved. Thus, the probability of cross protection appears to be more favourable. As a result, H5 and/or H7, most preferably H5 of avian influenza virus, are used as antigen for the preparation of the pharmaceutical composition.

The term "hemagglutinin5 (H5)" or "H5 of the of avian influenza virus" as used herein means but is not limited to any naturally occurring H5 and any modified forms of H5, including any deletion, substitution and/or insertion mutant of H5. It furthermore means any antigenic part of H5, which means any peptide-fragment which shows antigenic properties in an standard hemagglutinin inhibition assay. Normally said antigenic part thereof comprises 35, 30, 25, 20, 18, 15, 13, 10, 9, or most preferably 8 contiguous amino acids of the amino acid sequence that encodes for the H5, modified or non-modified, which shows antigenic properties in an standard hemagglutinin inhibition assay. An standard hemagglutinin inhibition assay for example is described in Stephenson et al., Virus Research vol. 103, pp. 91-95 (2004) with further references or described in the Examples. In case of questionable results, the HI assay as described in Example 2 shall be understood to be the relevant reference assay in connection with all aspects of the invention as described herein.

Preferred H5 antigens that can be used according to the invention include any modified H5 antigens that shows higher antigenic properties as compared to a non-modified H5, wherein the antigenic property is measured in a standard hemagglutinin inhibition assay, for example as described in Example 2. Briefly, HI assay was performed to detect the presence of HA-specific antibodies. A heterologous H5N1 virus, A/chicken/Mexico/232/94, was used at a concentration of four hemagglutinating units [4 HA units] in the HI assay. In U-bottomed microtiter plates serial two-fold serum dilutions in PBS were subsequently mixed with equal volumes (25 µl) containing 4 HA units of virus, and incubated at 37° C. for one hour. Chicken red blood cells, at a concentration of 0.5% in PBS, were added to the serum-virus containing wells and incubated for 40 min at room temperature. The HI titers were determined as reciprocals of the highest serum dilutions in which inhibition of hemagglutination was observed.

Of note, Haesebrouck and Pensaert (1986) found "that there may exist a correlation between the HI titers against the challenge virus and protection from challenge". Haesebrouck and Pensaert (1986) also determined that pigs with HI titers of ≥40 were "completely resistant to challenge and no replication of the virus occurred in the respiratory tract at challenge". Thus, the development of HI titers ≥40 in the vaccinated swine would correlate to protection. (F. Haesebrouck and M. B. Pensaert. 1986. Effect of intratracheal challenge of fattening pigs previously immunised with an inactivated influenza H1N1 vaccine (*Veterinary Microbiology*, 11 (1986) 239-249 239)9. It has to assume that equivalent or at least nearly equivalent H5 HI titers will also result in a complete immune protection of swine against avian influenza virus. Lower titers, at least result in a seroconversion of the vaccinated animals and result in partial immune protection of those animals, which also can dramatically reduce the risk of a pandemics.

More preferably, H5 antigens used according to the invention include modified H5 antigens, which show an increased antigenic property as compared to the H5 antigen encoded by the sequence of SEQ ID NO:2, wherein the antigenic property is measured in a standard hemagglutinin inhibition assay, for example as described in Lüschow et al., *Vaccine* 19 (2001), pp. 4249-4259 with further references. The term "higher or increased antigenic property" as used herein refers to a hemagglutinin inhibition that is at least 20%, preferably at least 50%, more preferably at least 75%, even more preferably at least 100% higher than that of the reference H5 antigen, i.e. the non modified H5 antigen or the H5 antigen having the sequence of SEQ ID NO:2.

Furthermore preferred H5 antigens that can be used according to the invention include H5 antigens which comprise a peptide that comprises i. the amino acid sequences of SEQ ID NO:1, SEQ ID NO:2, SEQ ID NO:3; SEQ ID NO:4; SEQ ID NO:5 or SEQ ID NO:6 or;

ii. any peptide that has at least 85% sequence homology, more preferably at least about 90% sequence homology, still more preferably at least about 95% sequence homology, even more preferably at least about 97% sequence homology, still even more preferably at least about 98% sequence homology, and even more preferably at least about 99% sequence homology to the polypeptide of i) that comprises hemagglutinin inhibition in a standard hemagglutinin inhibition as described above; or iii. any antigenic part of the polypeptides of i) or ii) comprising at least 35, 30, 25, 20, 18, 15, 13, 10, 9, or most preferably 8 contiguous amino acids of any of peptides of i) or ii).

iv. any peptides of i), ii) or iii) having the amino acids 223N, 36T/223N, 36K/223N, 83A/223N, 83T/223N, 83D/223N, 86A/223N, 86V/223N, 120N/223N, 120S/223N, 155N/223N, 155S/223N, 156A/223N, 156T/223N, 189R/223N, 189K/223N, 212K/223N, 212R/223N, 212E/223N, 223N/263A, 223N/263T, or 120N/155N/223N.

v. any peptide of i), ii), iii) or iv) having the amino acid 223N and one or more of the following amino acid clusters selected from the group consisting of:
    a. aa 93-95: GNF
    b. aa 123-125: SDH
    c. aa 128-130: SSG
    d. aa 138-140: GSS
    e. aa 226-228: MDF
    f. aa 270-272: EVE
    g. aa 309-311: NKL; or vi. any peptide of i), ii) iii) or iv) having the amino acid 223N and one or more of the following amino acid clusters selected from the group consisting of:
    a. aa 93-95: GNF
    b. aa 128-130: SSG
    c. aa 138-140: GSS.

Furthermore preferred H5 antigens that can be used according to the invention include H5 antigens which comprise the peptides provided in the table 1, or any immunogenic part thereof:

TABLE 1

H5 antigens

| Sequence name | Basic-sequence | Amino acid positions# | | | | | | | | | |
|---|---|---|---|---|---|---|---|---|---|---|---|
| | | 36 | 83 | 86 | 120 | 155 | 156 | 189 | 212 | 223 | 263 |
| 223N | any HA H5 | — | — | — | — | — | — | — | — | N | — |
| 36T/223N | any HA H5 | T | — | — | — | — | — | — | — | N | — |
| 36K/223N | any HA H5 | K | — | — | — | — | — | — | — | N | — |
| 83A/223N | any HA H5 | — | A | — | — | — | — | — | — | N | — |
| 83T/223N | any HA H5 | — | T | — | — | — | — | — | — | N | — |
| 83D/223N | any HA H5 | — | D | — | — | — | — | — | — | N | — |
| 86A/223N | any HA H5 | — | — | A | — | — | — | — | — | N | — |
| 86V/223N | any HA H5 | — | — | V | — | — | — | — | — | N | — |
| 120N/223N | any HA H5 | — | — | — | N | — | — | — | — | N | — |
| 120S/223N | any HA H5 | — | — | — | S | — | — | — | — | N | — |
| 155N/223N | any HA H5 | — | — | — | — | N | — | — | — | N | — |
| 155S/223N | any HA H5 | — | — | — | — | S | — | — | — | N | — |
| 156A/223N | any HA H5 | — | — | — | — | — | A | — | — | N | — |
| 156T/223N | any HA H5 | — | — | — | — | — | T | — | — | N | — |
| 189R/223N | any HA H5 | — | — | — | — | — | — | R | — | N | — |
| 189K/223N | any HA H5 | — | — | — | — | — | — | K | — | N | — |
| 212K/223N | any HA H5 | — | — | — | — | — | — | — | K | N | — |
| 212R/223N | any HA H5 | — | — | — | — | — | — | — | R | N | — |
| 212E/223N | any HA H5 | — | — | — | — | — | — | — | E | N | — |
| 223N/263A | any HA H5 | — | — | — | — | — | — | — | — | N | A |
| 223N/263T | any HA H5 | — | — | — | — | — | — | — | — | N | T |
| 120N/155N/223N | any HA H5 | — | — | — | N | N | — | — | — | N | — |
| A/duck/China/E319-2/03 | AAR99628 | T | A | A | S | D | A | R | K | S | A |
| A/duck/China/E319-2/03 | AAR99628 | T | A | A | S | D | A | R | K | S | A |
| A/duck/China/E319-2/03_223N | AAR99628 | T | A | A | S | D | A | R | K | N | A |
| A/duck/China/E319-2/03_120N/223N | AAR99628 | T | A | A | N | D | A | R | K | N | A |
| A/duck/China/E319-2/03_155N/223N | AAR99628 | T | A | A | S | N | A | R | K | N | A |
| A/duck/China/E319-2/03_120N/155N/223N | AAR99628 | T | A | A | S | N | N | R | K | N | A |
| HA/HK/213/03 | AY518362 | T | A | A | N | N | A | R | K | N | A |
| HA/Vietnam/1203/04 | | K | T | V | S | S | T | K | R | S | T |
| HA/Vietnam/1203/04_223N | | K | T | V | S | S | T | K | R | N | T |
| HA//Vietnam/3046/04 | | T | A | V | S | S | T | K | R | S | T |
| HA//Vietnam/3046/04_223N | | T | A | V | S | S | T | K | R | N | T |
| HA/Vietnam/3062/04 | | T | A | V | S | S | T | K | R | S | T |
| HA/Vietnam/3062/04_223N | | T | A | V | S | S | T | K | R | N | T |
| HA/chicken/Vietnam/39/04 | | T | A | V | S | S | T | K | R | S | T |
| HA/chicken/Vietnam/39/04_223N | | T | A | V | S | S | T | K | R | N | T |
| HA/falcon/HK-D0028/04 | | T | A | A | S | S | A | K | E | S | A |
| HA/falcon/HK-D0028/04_223N | | T | A | A | S | S | A | K | E | N | A |
| HA/duck/Singapore/3/97 | | T | D | V | S | N | A | K | E | S | A |
| HA/duck/Singapore/3/97_223N | | T | D | V | S | N | A | K | E | N | A |
| HA/HK/156/97 | | T | A | A | S | S | A | K | E | S | T |
| HA/HK/156/97 | | T | A | A | S | S | A | K | E | N | T | the amino acid positions given in TABLE 1 refers to the positions as exemplarily defined in SEQ ID NO: 1. In other words amino acid 223 of TABLE 1 refers to the amino acid 223 of the sequence of SEQ ID NO: 1.
— means that the amino acids at this positions are variable as compared to the reference sequence.

Furthermore preferred H5 antigens that can be used according to the invention include H5 antigens which comprise
  i. a peptide having the sequences of NCBI Accession No. AAT65209, CAJ32556, ABC47656, CAF21874, CAF21870, AAC58998, AAC58997, AAC58996, AAC58994, AAC58993, AAC58992, AAC58991, AAC58990, AAC58995, AAS45134, AAN17270, AAN17269, AAN17268, AAN17267, AAN17266, AAN17265, AAN17264, AAN17263, AAN17262, AAN17261, AAN17260, AAN17259, AAN17257, AAN17256, AAN17255, AAN17254, AAA43083, AAA43082, AAB19079, BAE48696, BAE48693, BAE48696, BAE48695, BAE48694, BAE48692, BAE48691, BAE48690, BAE48689, BAE48688, BAE48687, BAE48686, BAE48685, BAE48684, BAE48683, AAC58999, ABC72082, AAV91149, AAP71993, AAP71992, AAP71991, AAP71990, AAP71989, AAP72011, AAP72010, AAP72009, AAP72008, AAP72007, AAP72006, AAP72005, AAP72004, AAP72003, AAP72002, AAP72001, AAP72000, AAP71999, AAP71998, AAP71997, AAP71996, AAP71995, AAP71994, AAF99718, ABF58847, AAG38534, AAC32102, AAC32099, AAL75847, AAC32101, AAC32098, AAC32088, AAC32078, AAR99628, AAC32100, AAM49555, AAL75843, AAL75839, AAD13573, AAD13568, AAF04720, AAF04719, AAC34263, AAR16155, AAD13574, AAD13570, AAD13575, AAD13572, AAD13569, AAD13567, AAD13566, AAK57506, AAG01225, AAG01215, AAG01205, AAG01195, or ABD83813, or
  ii. any peptide that has at least 85% sequence homology, more preferably at least about 90% sequence homology, still more preferably at least about 95% sequence homology, even more preferably at least about 97% sequence homology, still even more preferably at least about 98% sequence homology, and even more preferably at least about 99% sequence homology to the polypeptide of i) and that show hemagglutinin inhibition in a standard hemagglutinin inhibition as described above;

iii. any of the peptides of i) or ii) having the amino acids 223N, 36T/223N, 36K/223N, 83A/223N, 83T/223N, 83D/223N, 86A/223N, 86V/223N, 120N/223N, 120S/223N, 155N/223N, 155S/223N, 156A/223N, 156T/223N, 189R/223N, 189K/223N, 212K/223N, 212R/223N, 212E/223N, 223N/263A, 223N/263T, or 120N/155N/223N; or iv. any antigenic part of the peptides of i), ii) comprising at least 35, 30, 25, 20, 18, 15, 13, 10, 9, or most preferably 8 contiguous amino acids of any of such peptides of i), ii) or iii); or v. any of such antigenic parts of iv), wherein those antigenic parts comprise the amino acid 223 of H5; or vi. any of such antigenic parts of v) wherein those antigenic parts comprise the amino acid 223N; or vii. any of such peptides of i), ii), iii), iv), v) or vi) having the amino acid 223N and one or more of the following amino acid clusters selected from the group consisting of:
  h. aa 93-95: GNF
  i. aa 123-125 SDH
  j. aa 128-130: SSG
  k. aa 138-140: GSS
  l. aa 226-228: MDF
  m. aa 270-272: EVE
  n. aa 309-311: NKL; or viii. any peptide of i), ii) iii) or iv) having the amino acid 223N and one or more of the following amino acid clusters selected from the group consisting of:
  d. aa 93-95: GNF
  e. aa 128-130: SSG
  f. aa 138-140: GSS "Sequence homology", as used herein, refers to a method of determining the relatedness of two sequences. To determine sequence homology, two or more sequences are optimally aligned, and gaps are introduced if necessary. In contrast to sequence identity, conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferred of 100, even more preferred of 250, even more preferred of 500 nucleotides. Upon such alignment, sequence homology is ascertained on a position-by-position basis, e.g., the sequences are "homolog" at a particular position if at that position, the nucleotides or amino acid residues are identical. The total number of such position identities is then divided by the total number of nucleotides or amino acid residues in the reference sequence to give % sequence homology. Sequence homology can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence homology are designed to give the largest match between the sequences tested. Methods to determine sequence homology are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence homology between the given and reference sequences.

Furthermore preferred H5 antigens that can be used according to the invention, are i. any of those mentioned supra having the amino acid 223N and the modification 328K+;

ii. any of those mentioned supra having the amino acid 94N/223N and the modification 328K+;

iii. any H5 antigen of avian origin having the amino acid 223N, and the modification 328K+, wherein avian origin means that the H5 sequence derived form a virus isolate that was originally isolated from a poultry infected with avian influenza virus type 5; or iv. any H5 antigen of avian origin having the amino acids 94N/223N and the modification 328K+, wherein avian origin means that the H5 sequence derived form a virus isolate that was originally isolated from a poultry infected with avian influenza virus type 5; or.

v. any H5 antigen of avian origin having the amino acids 155N/223N and the modification 328K+, wherein avian origin means that the H5 sequence derived form a virus isolate that was originally isolated from a poultry infected with avian influenza virus type 5; or vi. any H5 antigen of avian origin having the amino acid 120N/155N/223N and the modification 328K+, wherein avian origin means that the H5 sequence derived form a virus isolate that was originally isolated from a poultry infected with avian influenza virus type 5; or vii. any H5 antigen having the modifications 94N/223N and the modification 328K+; or viii. any H5 antigen having the modifications 94N/155N/223N and the modification 328K+; or;

ix. any H5 antigen having the modifications 94N/120N/155N/223N and the modification 328K+; or x. any H5 having the modifications 223N/the modification 328K+, and one or more of the following amino acid clusters selected from the group consisting of:
  a. aa 93-95: GNF
  b. aa 123-125: SDH
  c. aa 128-130: SSG
  d. aa 138-140: GSS
  e. aa 226-228: MDF
  f. aa 270-272: EVE
  g. aa 309-311: NKL; or xi. any H5 antigen having the amino acid 223N, and the modification 328K+, and one or more of the following amino acid clusters selected from the group consisting of:
  a. aa 93-95: GNF
  b. aa 128-130: SSG
  c. aa 138-140: GSS; or
xii. any H5 antigen having the amino acid sequence of SEQ ID NO:4.

Furthermore preferred H5 antigens that can be used according to the invention to the invention include H5 antigens as described by Hoffmann et al, *PNAS, vol.* 106, no. 36, pp. 12915-12920 of Sep. 6, 2005. The disclosure of this reference shall be entirely included herein by reference.

The numbering of the amino acid positions of the H5 protein as used herein, refers to the amino acid position as exemplarily given in SEQ ID NO:1. SEQ ID NO:1 represents the amino sequence of the hemagglutinin of strain duck/China/E319-2/03 but lacking the signal peptide. In other words, if reference is made to the amino acid at position 223 (amino acid 223), the amino acid residue is meant which corresponds to amino acid 223 of SEQ ID NO:1. In the current case, amino acid 223 would be Serine (S). The terms "223N", or "155N" exemplarily mean, that at amino acid positions 223 and 155, respectively—numbering according to the amino acid positions of SEQ ID NO:1—, shall code for the amino acid Asparagine (N). In other words, if reference is made to "H5 antigen having the amino acid 223N", a H5 amino acid molecule that normally codes for Serine at amino acid position 223—numbering according to the amino acid positions of SEQ ID NO:1—that amino acid shall be substituted by an Asparagine (N). The term "328K+" or "modification 328K+" means, that at amino acid position 328 of H5 antigen—numbering according to the amino acid positions of SEQ ID NO:1—, a second Lysine (K+) is inserted. In cases were amino acids sequences at positions 328 and 329 naturally codes for Lysine-Lysine, no further Lysine (K) shall be inserted. However, most of the known H5 sequences code at amino acid positions 328 and 329 for Lysin-Argenine. In any such cases, the term 328K+ modification means, that a second Lysine (K) shall be inserted between Lysine at position 328 and Argenin at position 329. The modified sequence would read then Lysine-Lysine-Argenine (KKR).

It is also in the meaning of the present invention, that any other antigen, particularly any H and N antigen, can be used in a modified or non-modified version. As mentioned with respect to H5 antigen, most preferred are modified antigens, showing a high antigenic property in a standard hemaglutinin inhibition assay as compared to the non-modified antigens.

Methods, of how to introduce any of the above-mentioned modifications within the nucleotide sequence of an influenza virus are well known in the art. The genomic sequence of the entire influenza virus can be modified according to the invention, for example according to the methods described in U.S. Pat. No. 6,951,754, with further references.

Furthermore there may be employed conventional molecular biology, microbiology, and recombinant DNA techniques within the skill of the art to modify a nucleic acid sequence encoding for an antigen as described herein. Such techniques are explained fully in the literature. See, e.g., Sambrook et al., *Molecular Cloning: A Laboratory Manual, Second Edition* (1989) Cold Spring Harbor Laboratory Press, Cold Spring Harbor, N.Y.; *DNA Cloning: A Practical Approach, Volumes I and II* (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. 1994).

The immune response against a hemagglutinin antigen, e.g. H5 in an vaccinated animal can be measured by standard methods well know in the art, for example as described in Example 2. Briefly, serum antibody titers, mainly those determined by hemagglutinin inhibition (HI) and/or virus neutralization assays, are accepted surrogate measures of immune protection. Standard HI and virus neutralization assays can be performed in Madin Darby canine kidney cells as described Palmer et al., 1975, *Advanced Laboratory Techniques for Influenza Diagnosis*, U.S. Department of Health, Education and Welfare, Washington, D.C. and/or Kida et al., 1982, *Virology*, vol. 122, pp. 38-47. The reference test used in respect to the current invention is described in Lüschow et al., *Vaccine* 19 (2001), pp. 4249-4259 with further references. As already mentioned above, in case of questionable results, the HI assay as described in Example 2 shall be understood to be the relevant reference assay in connection with all aspects of the invention as described herein.

According to a further general aspect, the present invention relates to the use of an antigenic composition that comprises an antigen of a pathogen of an animal of a first species for the preparation of a pharmaceutical composition for the immunization of an animal of a second species, characterized in that the administration of a pharmaceutical composition, that comprises an antigen of a pathogen of an animal of a first species, to an animal of the second species results in a reduction or absence of the replication of a pathogen, that is infectious to an animal of the first species, in an animal of the second species, when said animal of the second species is infected with the infectious pathogen of the animal of the first species, provided that the antigen of the antigenic composition of the pharmaceutical composition is present in or on the infectious pathogen. The term "replication" as used herein means among others, the doubling/multiplication of the genome of the pathogen. The meaning the term reduction of the replication is described supra.

According to a further general aspect, the present invention relates to the use of an antigenic composition that comprises an antigen of a pathogen of an animal of a first species for the preparation of a pharmaceutical composition for the immunization of an animal of a second species, characterized in that the administration of the pharmaceutical composition, that comprises an antigen of a pathogen of an animal of a first species, to the animal of the second species results in prevention from adaptation of the infectious pathogen of the first animal to the second animal, when the animal of the second species is infected with said infectious pathogen of the animal of the first species. The term "adaption" as used herein, means among others, that the pathogen is adapted to the replication in the new species, which means, that the pathogen has overcome the species hurdles. The species hurdle is deemed to be overcome, if the pathogen spreads vertically, which means from animal-to-animal of the same species (also called: interspecies transmission or vertical transmission).

According to a further aspect, the invention relates to the use of the hemagglutinin H1, H3, H5, H7 and/or H9 of the avian influenza virus for the preparation of a pharmaceutical composition for the administration to a pig, wherein said pharmaceutical composition, when administered to a pig, results in a reduction or absence of the reproduction of an infectious avian influenza virus of subtype H1, H3, H5, H7 or H9 in a pig, when infected with said infectious avian influenza virus of subtype H1, H3, H5, H7 or H9. Most preferred is the use of antigen H5 and/or H7.

According to a further aspect, the invention relates to the use of the hemagglutinin H1, H3, H5, H7 and/or H9 of the avian influenza virus for the preparation of a pharmaceutical composition, when administered to a pig, results in prevention from adaptation of an infectious avian influenza virus of subtype 5 from avian to pig, when infected with said infectious avian influenza virus of subtype H1, H3, H5, H7 or H9. Most preferred is the use of antigen H5 and/or H7. According to a further aspect, use of the hemagglutinin H5 and/or, H7 of the avian influenza virus for the preparation of said pharmaceutical composition is even more preferred.

According to a further aspect, the present invention relates to the use of an pharmaceutical composition comprising an antigen of avian influenza virus of subtypes H1, H3, H5, H7 and/or H9 for the preparation of a vaccine for the treatment and/or prevention of an animal against the avian influenza. Preferably, the antigen to be used is H1, H3, H5, H7, and/or H9 of the avian influenza virus. More preferred the antigen to be used is the H5, and/or H7 of the avian influenza virus. According to further aspect of this embodiment, the animal to be treated are poultry, e.g, birds, ducks or gooses. According to further aspect of the invention, animals to be treated are mammals, preferably, pigs, cattle, horses, seals, camels, dogs, cats, hamsters, mice, or humans.

According to a further aspect, the present invention relates to a method for the prevention of the transmission of a pathogen of an animal of a first species to an animal of a second species, characterized in that antigen of a pathogen of an animal of the first species is used for the immunization of an animal of the second species against said pathogen of the animal of the first species, wherein the administration of said antigen results in the reduction or the absence of the reproduction of said pathogen of the animal of the first species in an animal of the second species.

According to a further embodiment of the method described supra, the first species is poultry. According to a further aspect of said method, the animal of second species is a mammal, preferably a pig, cattle, horse, seal, camel, dog, cat, hamster, mouse or human, most preferred a pig. The antigens according to this methods, are those described supra. Preferably said antigen is a microorganism or an antigenic part and/or preparation of said microorganism. More preferred, said microorganism is of viral origin, even more preferred said microorganism is the avian influenza virus.

The pathogens of the animal of the first species preferably are those mentioned supra. Briefly, such pathogen is the avian influenza virus. According to a further aspect, said pathogen is the avian influenza virus of subtype H1, H3, H5, H7 or H9. More preferred, said pathogen is the avian influenza virus of subtype H5N1.

According to a further aspect, the present invention relates to a method for the prevention of the transmission of a pathogen of an animal of a first species to an animal of a second species, characterized in that antigen of a pathogen of an animal of a first species is used for the immunization of an animal of a second species against the pathogen of the animal of the first species, wherein the administration of said antigen results in the reduction or the absence of the reproduction of pathogen of the animal of the first species in an animal of the second species, wherein the antigen is the hemagglutinin (H) and/or the neuraminidase (N) of influenza virus, preferably of avian origin. According to a further aspect of said method, the antigen is the H1, H3, H5, H7, and/or H9 of the avian influenza virus, whereas H5 and/or H7 are more preferred. A more detailed description of those antigens is found supra.

According to a further important aspect, the present invention relates to a method for the prevention of the transmission of a pathogen of an animal of a first species to human, characterized in that an antigen of a pathogen of an animal of a first species is used for the immunization of an animal other than human of a second species, that is not a against the pathogen of the animal of the first species, wherein the administration of the antigen results in the reduction or the absence of the reproduction of pathogen of the animal of the first species in said animal of the second species. Preferably, the first species is poultry, e.g. bird, chicken, duck, etc., and the animal of the second species is a mammal other than human, preferably pig, cattle, horse, seal, camel, dog, cat, hamster, mouse, most preferred pig.

The pathogens of the animal of the first species preferably are those mentioned supra. Briefly, such pathogen is the avian influenza virus. According to a further aspect, said pathogen is the avian influenza virus of subtype H1, H3, H5, H7 or H9. More preferred, said pathogen is the avian influenza virus of subtype H5N1.

According to a further aspect, the present invention relates to a method for the prevention of the transmission of a pathogen of an animal of a first species to human, characterized in that antigen of a pathogen of an animal of a first species is used for the immunization of an animal of the second species against the pathogen of the animal of the first species, wherein the administration of said antigen results in the reduction or the absence of the reproduction of pathogen of the animal of the first species in an animal of the second species, wherein the antigen is the hemagglutinin (H) and/or the neuraminidase (N) of influenza virus, preferably of avian origin. According to a further aspect of said method, the antigen is the H1, H3, H5, H7, and/or H9 of the avian influenza virus, whereas H5 and/or H7 are more preferred. A more detailed description of those antigens is found supra.

A further aspect of the present invention relates to a method for the prevention or reduction of recombination between pathogens of an animal of a first species and an animal of a second species in an animal, wherein a pharmaceutical composition comprising antigen of the pathogen of an animal of the first species is used for the immunization of animals of the second species against the pathogen of the animal of the first species. The recombination event is often responsible for overcoming of the species hurdles. Reduction or prevention of these recombination events would reduce the risk for overcoming the species hurdles. The species hurdle is deemed to be overcome, if the pathogen spreads vertically, which means from animal-to-animal of the same species (also called: inter-species transmission or vertical transmission)

Preferably, the pathogens are of the family or genus. More preferably, those pathogens are viruses, preferably influenza viruses. According to a further embodiment of this method, the first pathogen is avian influenza virus and the second pathogen is a mammalian influenza virus. Moreover, if the first pathogen is avian influenza virus and the second pathogen is a mammalian influenza virus, a preferred pharmaceutical composition comprises antigen of avian influenza virus H1, H3, H5, H7, and/or H9, even more preferred H5 and/or H7.

According to a further aspect, the invention relates to a method for the reduction or prevention recombination between a pathogen of an animal of a first species and a pathogen of an animal of a second species in an animal, wherein a pharmaceutical composition comprising antigen of the pathogen of an animal of the first species is used for the immunization of an animal of the second species against the pathogen of the animal of the first species, and wherein the administration of said antigen results in the reduction or the absence of the reproduction of pathogen of the animal of the first species in an animal of the second species. Preferably, those pathogens are of the family or genus. More preferably, those pathogens are viruses, preferably influenza viruses. Moreover, if the first pathogen is avian influenza virus and the second pathogen is a mammalian influenza virus, a preferred pharmaceutical composition comprises antigen of avian influenza virus H1, H3, H5, H7, and/or H9, even more preferred H5 and/or H7.

The antigen(s), antigenic composition(s) as used according to the invention, can be made in a recombinant manner, for example by the use of the baculovirus expression system in insect cells. Further examples of well established recombinant expression systems are bacterial expression systems such as *E. coli* or *B. subtilis*, yeast-based expression systems such as *S. cerevisiae* or *S. pombe*, or mammalian cell expression systems such as the BHK-, CHO- and/or NS0-based expression systems. Such systems are well known in the art and generally available, e.g. commercially through Clontech Laboratories, Inc. 4030 Fabian Way, Palo Alto, Calif. 94303-4607, USA. Further expression strategies are for example described in Lüschow et al., *Vaccine* no. 19 (2001), pp. 4249-4259, or Veit et al., *PNAS* vol. 103 (2006), pp. 8197-8202. Furthermore, recombinant adeno-associated virus systems are well established and for example described in U.S. Pat. No. 5,436,146 or WO200203872 with further references. Moreover, vaccinia (pox) virus based expression systems, for example as described in U.S. Pat. No. 6,265,183 with further references, are also well established and suitable to produce recombinant antigen(s), antigenic composition(s) as used according to the invention. Further suitable expression systems make use of recombinant popova viruses, such as SV40, fowl pox virus, pseudorabies viruses and retroviruses.

According to a furthermore preferred aspect of the present invention, the antigen(s) or at least one antigen is/are produced in insect cells by using the baculovirus expression system. More preferably, the recombinant baculovirus encodes for the antigen and produce the antigen. Thus, according to a further aspect of the invention, the antigens H1, H3, H5, H7 and/or H9 of avian influenza virus are coded and produced by the recombinant baculovirus.

However, the relevant antigen(s), antigenic composition(s), can also be inactivated virus comprising antigen, an apathogenic version of a live virus comprising an antigen, preparation and/or fragments of a virus, wherein said preparation and/or fragment comprising antigen(s).

Another important aspect of the present invention is the preparation of the pharmaceutical compositions such as vaccines, which comprises at least one antigen of a pathogen as described above. The skilled person knows additional components which may be comprised in said compositions/vaccines together with antigen (see for example, *Remington's Pharmaceutical Sciences*. (1990). 18th ed. Mack Publ., Easton). The expert may use known injectable, physiologically acceptable sterile solutions. For preparing a ready-to-use solution, aqueous isotonic solutions, such as e.g. saline or corresponding plasma protein solutions are readily available. The pharmaceutical composition/vaccine may be present as lyophylisates or dry preparations, which can be reconstituted with a known injectable solution directly before use under sterile conditions, e.g. as a kit of parts.

In addition, the pharmaceutical/vaccine compositions of the present invention can include one or more veterinary-acceptable carriers. As used herein, "a veterinary-acceptable carrier" includes but is not limited to any and all solvents, dispersion media, coatings, adjuvants, stabilizing agents, diluents, preservatives, antibacterial and antifungal agents, isotonic agents, adsorption delaying agents, and the like.

Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion.

The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997). Examples for suitable oil-in water emulsions are Emulsigen-based adjuvants, such as EMULSIGEN®, EMULSIGEN-D®, EMULSIGEN-P®, EMULSIGEN-75® (MVP Laboratories, Inc. Omaha, Nebr., USA). It has been surprisingly found, that pharmaceutical/vaccine compositions that comprise H5 antigen, preferably recombinant H5 antigen were effectivley adjuvanted with oil-in water emulsions, preferably with such Emulsigen-based adjuvants, more preferably with EMULSIGEN® and EMULSIGEN-P®.

Moreover, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971 P. Most preferred is the use of Cabopol 971 P. Among the copolymers of maleic anhydride and alkenyl derivative, the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, or muramyl dipeptide among many others.

Preferably, the adjuvant is added in an amount of about 100 µg to about 10 mg per dose. Even more preferred the adjuvant is added in an amount of about 100 µg to about 10 mg per dose. Even more preferred the adjuvant is added in an amount of about 500 µg to about 5 mg per dose. Even more preferred the adjuvant is added in an amount of about 750 µg to about 2.5 mg per dose. Most preferred the adjuvant is added in an amount of about 1 mg per dose.

The pharmaceutical/vaccine compositions, can further include one or more other immunomodulatory agents such as, e.g., interleukins, interferons, or other cytokines. The pharmaceutical/vaccine compositions can also include Gentamicin and Merthiolate. While the amounts and concentrations of adjuvants and additives useful in the context of the present invention can readily be determined by the skilled artisan, the present invention contemplates compositions comprising from about 50 ug to about 2000 ug of adjuvant and preferably about 250 ug/1 ml dose of the vaccine composition. In another preferred embodiment, the present invention contemplates vaccine compositions comprising from about 1 ug/ml to about 60 ug/ml of antibiotics, and more preferably less than about 30 ug/ml of antibiotics.

Administration strategies for influenza vaccines are well known in the art. Mucosal vaccination strategies for inactivated and attenuated virus vaccines are contemplated. While the mucosa can be targeted by local delivery of a vaccine, various strategies have been employed to deliver immunogenic proteins to the mucosa.

In a specific embodiment, the vaccine can be administered in an admixture with, or as a conjugate or chimeric fusion protein with, cholera toxin, such as cholera toxin B or a cholera toxin A/B chimera (Hajishengallis, *J Immunol.*, 154: 4322-32, 1995; Jobling and Holmes, *Infect Immun.*, 60:4915-24, 1992). Mucosal vaccines based on use of the cholera toxin B subunit have been described (Lebens and Holmgren, *Dev Biol Stand* 82:215-27, 1994). In another embodiment, an admixture with heat labile enterotoxin (LT) can be prepared for mucosal vaccination.

Other mucosal immunization strategies include encapsulating the virus in microcapsules (U.S. Pat. No. 5,075,109, U.S. Pat. No. 5,820,883, and U.S. Pat. No. 5,853,763) and using an immunopotentiating membranous carrier (WO 98/0558). Immunogenicity of orally administered immunogens can be enhanced by using red blood cells (rbc) or rbc ghosts (U.S. Pat. No. 5,643,577), or by using blue tongue antigen (U.S. Pat. No. 5,690,938).

EXAMPLES

The following examples set forth preferred materials and procedures in accordance with the present invention. It is to be understood, however, that these examples are provided by way of illustration only, and nothing therein should be deemed a limitation upon the overall scope of the invention.

Example 1

Construction of a Recombinant Baculoviruses Coding for and Expressing HA H5 Antigens The recombinant baculovirus containing the H5 HA antigen was generated as follows: the coding sequences of the H5 HA (SEQ ID NO:2) was chemically synthesized and subcloned into the transfer vector pVL1392 (BD Biosciences Pharmingen, San Diego, Calif.). The H5 HA MutK+ (SEQ ID NO:4) was generated by using oligonucleotide primers and the QuikChange® Site-Directed Mutagenesis Kit (Stratagene, La Jolla, Calif.) and subcloned into the transfer vector pVL1392 (BD Biosciences Pharmingen, San Diego, Calif.). The pVL1392 plasmids containing the genes coding for H5 HA antigen (SEQ ID NO:2) and H5 HA MutK+ (SEQ ID NO:4) were then co-transfected with DiamondBac® (Sigma) baculovirus DNA into Sf9 insect cells (BD Biosciences Pharmingen) to generate the recombinant baculovirus containing the genes H5 HA coding for SEQ ID NO:2 and H5 HA mutK+ coding for SEQ ID NO:4. The recombinant baculoviruses containing the genes coding for H5 HA (SEQ ID NO:2) and H5 HA MutK+ (SEQ ID NO:4) were plaque-purified and Master Seed Viruses (MSVs) were propagated on the SF9 cell line, aliquoted, and stored at −70° C. Insect cells infected with H5 HA baculoviruses as described above to generate MSV or Working Seed Viruses express H5 HA antigen (SEQ ID NO:2) and H5 HA MutK+ (SEQ ID NO:4) antigen as detected by polyclonal serum or monoclonal antibodies in an indirect fluorescent antibody assay or Western blot.

After being seeded with the appropriate amounts of recombinant baculoviruses (H5 HA and H5 HA MutK+, respectively), spinner flasks containing SF+ cells (Protein Sciences, Inc., Meriden, Conn.) were then incubated at 27±2° C. for 7 days and with stirring 100 rpm during that time. The flasks used ventilated caps to allow for air flow. The crude whole cell culture containing baculovirus infected SF+ cells and the cell culture supernants of each culture were harvested.

Example 2

Preparation of Pharmaceutical Compositions (Vaccines) Comprising HA H5 Antigens

The crude whole cell H5 HA protein and H5 HA Mutk+ protein expressed in insect cells by baculovirus-based expression system were harvested. Baculoviruses were inactivated in the presence of 5 mM cyclized binary ethylenimine (BEI) (final concentration) between about 32 and 39° C. for 72 to 96 hours. After inactivation is completed a 0.3 M sodium thiosulfate solution was added to a final concentration of 5 mM to neutralize any residual BEI. After neutralization various adjuvants were added and the following vaccine/pharmaceutical compositions were generated.

Vaccines

| Generic product name | 501 |
|---|---|
| Antigen | Crude whole-cell H5 HA protein expressed in insect cells by a baculovirus-based expression system. |

| | | |
|---|---|---|
| Formulation | An experimental vaccine comprised of cultured insect cells and supernatant expressing recombinant H5 HA. The vaccine was adjuvanted with Emulsigen. | |
| Generic product name | 502 | |
| Antigen | Crude whole-cell H5 HA protein expressed in insect cells by a baculovirus-based expression system. | |
| Formulation | An experimental vaccine comprised of cultured insect cells and supernatant expressing recombinant H5 HA. The vaccine was adjuvanted with Emulsigen-D. | |
| Generic product name | 503 | |
| Antigen | Crude whole-cell H5 HA protein expressed in insect cells by a baculovirus-based expression system. | |
| Formulation | An experimental vaccine comprised of cultured insect cells and supernatant expressing recombinant H5 HA. The vaccine was adjuvanted with Polygen. | |
| Generic product name | 504 | |
| Antigen | Crude whole-cell H5 HA protein expressed in insect cells by a baculovirus-based expression system. | |
| Formulation | An experimental vaccine comprised of cultured insect cells and supernatant expressing recombinant H5 HA. The vaccine was adjuvanted with Emulsigen-P. | |
| Generic product name | 505 | |
| Antigen | Crude whole-cell H5 HA protein expressed in insect cells by a baculovirus-based expression system. | |
| Formulation | An experimental vaccine comprised of cultured insect cells and supernatant expressing recombinant H5 HA. The vaccine was adjuvanted with Carbigen. | |
| Generic product name | 506 | |
| Antigen | Crude whole-cell H5 HA protein expressed in insect cells by a baculovirus-based expression system. | |
| Formulation | An experimental vaccine comprised of cultured insect cells and supernatant expressing recombinant H5 HA. The vaccine was adjuvanted with Emulsigen-75. | |
| Generic product name | 507 | |
| Antigen | Crude whole-cell H5 HA protein expressed in insect cells by a baculovirus-based expression system. | |
| Formulation | An experimental vaccine comprised of cultured insect cells and supernatant expressing recombinant H5 HA. The vaccine was adjuvanted with ISA 70. | |
| Generic product name | 508 | |
| Antigen | Crude whole-cell H5 HA mutK+ protein expressed in insect cells by a baculovirus-based expression system. | |
| Formulation | An experimental vaccine comprised of cultured insect cells and supernatant expressing recombinant H5 HA. The vaccine was adjuvanted with Emulsigen. | |
| Generic product name | 509 | |
| Antigen | Crude whole-cell H5 HA mutK+ protein expressed in insect cells by a baculovirus-based expression system. | |
| Formulation | An experimental vaccine comprised of cultured insect cells and supernatant expressing recombinant H5 HA. The vaccine was adjuvanted with Emulsigen-D. | |
| Generic product name | 510 | |
| Antigen | Crude whole-cell H5 HA mutK+ protein expressed in insect cells by a baculovirus-based expression system. | |
| Formulation | An experimental vaccine comprised of cultured insect cells and supernatant expressing recombinant H5 HA. The vaccine was adjuvanted with Polygen. | |
| Generic product name | 511 | |
| Antigen | Crude whole-cell H5 HA mutK+ protein expressed in insect cells by a baculovirus-based expression system. | |
| Formulation | An experimental vaccine comprised of cultured insect cells and supernatant expressing recombinant H5 HA. The vaccine was adjuvanted with Emulsigen-P. | |
| Generic product name | 512 | |
| Antigen | Crude whole-cell H5 HA mutK+ protein expressed in insect cells by a baculovirus-based expression system. | |
| Formulation | An experimental vaccine comprised of cultured insect cells and supernatant expressing recombinant H5 HA. The vaccine was adjuvanted with Carbigen. | |
| Generic product name | 513 | |
| Antigen | Crude whole-cell H5 HA mutK+ protein expressed in insect cells by a baculovirus-based expression system. | |
| Formulation | An experimental vaccine comprised of cultured insect cells and supernatant expressing recombinant H5 HA. The vaccine was adjuvanted with Emulsigen-75. | |
| Generic product name | 514 | |
| Antigen | Crude whole-cell H5 HA K+ protein expressed in insect cells by a baculovirus-based expression system. | |
| Formulation | An experimental vaccine comprised of cultured insect cells and supernatant expressing recombinant H5 HA. The vaccine was adjuvanted with ISA 70. | |

Example 3

Vaccination of Swine (Pigs) Against Avian Influenza

1. Introduction

The purpose of this study was to determine the ability of experimental vaccines containing a crude extract of recombinant H5 hemagglutinin (HA) antigen to induce hemagglutination inhibition (HI) titers in swine. Various adjuvants were evaluated with the H5 HA antigens.

The HA H5 prototypes evaluated in this study contained antigen from either conventional H5 HA MutK+. Conventional H5 HA was derived from A/duck/China/E319-2/03, whereas H5 HA MutK+ consists of conventional H5 HA which was engineered to contain three specific amino acid changes at S120N, D150N, S223N and 328mutK+. It also contains amino acid 94N. The particular amino acid changes in H5 HA Mut K+ result in a H5 HA that more closely resembles the HA of A/HK/213/03. The amino acid composition of the H5 HA of A/HK/213/03 is currently thought to aid in antibody recognition of the H5 HA.

2. Study Design:

TABLE 1

Study Overview.

| Group | Number of Pigs | Vaccine Prototype | Day 0 | Day 21 | Day 35 |
|---|---|---|---|---|---|
| 1 | 5 | 501 | Bleed and Vaccinate Intramuscularly (brachiocephalic group) by administration of 1 ml in the LEFT side of the neck.) | Bleed and Vaccinate Intramuscularly (brachiocephalic group) by administration of 1 ml in the RIGHT side of the neck.) | Bleed and Terminate Study |
| 2 | 5 | 502 | | | |
| 3 | 5 | 503 | | | |
| 4 | 5 | 504 | | | |
| 5 | 5 | 505 | | | |
| 6 | 5 | 506 | | | |
| 7 | 5 | 507 | | | |
| 8 | 5 | 508 | | | |
| 9 | 5 | 509 | | | |
| 10 | 5 | 510 | | | |
| 11 | 5 | 511 | | | |
| 12 | 5 | 512 | | | |
| 13 | 5 | 513 | | | |
| 14 | 5 | 514 | | | |
| 15 | 5 | None | Bleed | Bleed | |

The piglets were 3 weeks ±5 days of age at the beginning of the study. The piglets were clinically healthy at the beginning of the study. Blood samples were obtained on Study Days 0, 21, and 35.

All study animals were observed daily on Study Days 1 through 35 in regard to the general health status. For seven days following each vaccination, injection sites were investigated daily and visible reactions were recorded. At the conclusion of the animal phase of the study on Study Day 35, all animals were humanely euthanized.

3. Vaccines

Vaccines 501 to 514 as described in EXAMPLE 2 were used for the pig vaccination study.

4. Hemagglutinin Inhibition Assay

Swine were vaccinated with the H5 HA-containing prototypes on Days 0 and 21. Swine sera were collected for evaluation by hemagglutination inhibition (HI) assay on Days 0, 21, 35. The HI assay was performed to detect the presence of HA-specific antibodies. A heterologous H5N1 virus, A/chicken/Mexico/232/94, was used at a concentration of four hemagglutinating units [4 HA units] in the HI assay. In U-bottomed microtiter plates serial two-fold serum dilutions in PBS were subsequently mixed with equal volumes (25 μl) containing 4 HA units of virus, and incubated at 37° C. for one hour. Chicken red blood cells, at a concentration of 0.5% in PBS, were added to the serum-virus containing wells and incubated for 40 min at room temperature. The HI titers were determined as reciprocals of the highest serum dilutions in which inhibition of hemagglutination was observed.

5. Results

HI test used the Mexican government official H5N1 antigen (A/chicken/Mexico/232/94) [4 HA Units] Vaccination regimen of 1×1 mL on Days 0 and 21.

TABLE 2

Results

| | | | HI Titers | | |
|---|---|---|---|---|---|
| | | | Day 0 | Day 21 | Day 35 |
| 501 | H5 - Emulsigen | | 0 | 0 | 4 |
| 502 | H5 - Emulsigen-D | | 0 | 0 | 4 |
| 503 | H5 - Polygen | | 0 | 0 | 0 |
| 504 | H5 - Emulsigen-P | | 0 | 0 | 2 |

TABLE 2-continued

Results

| | | HI Titers | | |
|---|---|---|---|---|
| | | Day 0 | Day 21 | Day 35 |
| 505 | H5 - Carbigen | 0 | 0 | 4 |
| 506 | H5 - Emulsigen-75 | 0 | 0 | 16 |
| 507 | H5 ISA 70 | 0 | 0 | 16 |
| 508 | H5 K+ - Emulsigen | 0 | 0 | 128 |
| 509 | H5 K+ - Emulsigen-D | 0 | 0 | 64 |
| 510 | H5 K+ - Polygen | 0 | 0 | 16 |
| 511 | H5 K+ - Emulsigen-P | 0 | 0 | 0 |
| 512 | H5 K+ - Carbigen | 0 | 0 | 0 |
| 513 | H5 K+ - Emulsigen-75 | 0 | 0 | 16 |
| 514 | H5 K+ - ISA 70 | 0 | 4 | 32 |
| Control | None | 0 | 0 | 0 |

BIV H5 (derived from Influenza A virus (A/duck/China/E319-2/03(H5N1))
BIV H5 K+ (mutated BIV H5 to include S120N, D155N, S223N, and added 328K+)

The results demonstrate that most of the vaccine compositions elicit an immune response in the vaccinated pigs. In particular, most of the vaccine compositions result in a seroconversion, which means most of the vaccinated pigs developed specific antibodies against the avian influenza virus used in the HI assay. Altogether, the results clearly and undoubtedly prove that the claimed inventive idea works very well. The risk of pendamic infection of pigs (animal of a second species), with avian influenza virus (pathogen of a first species) can dramatically be reduced by the vaccination of pigs with a relevant antigen of avian influenza virus. This has been clearly demonstrated. Moreover, by this vaccination concept, the transmission and adaption of avian influenza virus to mammals, including human beings is dramatically reduced. Pigs are one of the most important reservoirs for avian pathogens, including avian influenza virus. If the virus replication in pigs and therefore the risk of adaption of avian influenza to pigs is dramatically reduced and controlled, the risk for any adaption of avian influenza virus to human beings is also dramatically reduced. In case, where the administration of antigen results in lower HI titer, which means titer lower than 30, further boosts with antigen will be required to further improve the HI titer and to enhance the immune protection in the vaccinated pigs.

Therefore, low titer does not mean that no protection can be achieve, it only teach that further boosts seems to be required to improve the immune response. The fact, that an immune response could be measured in vaccinated pigs demonstrates the inventive idea underlying the present invention works very well. In other words, the experiments provided herewith clearly and undoubtedly give evidence that the inventive idea of the present invention works.

What is claimed is:

1. A method for reducing the transmission of avian influenza virus comprising administering an antigen of avian influenza virus subtype H5 to a nonhuman mammal, wherein the administration of the antigen of avian influenza virus subtype H5 results in a reduction of the reproduction of avian influenza virus in the non-human mammal, and reduces further transmission of the avian influenza virus to a second species of mammal from the non-human mammal, wherein the antigen of avian influenza virus subtype H5 comprises a modified SEQ ID NO: 4 comprising amino acids 17-568 of SEQ ID NO: 4 lacking the amino-terminal signal peptide.

2. The method according to claim 1, wherein modified SEQ ID NO: 4 is an adjuvanted recombinant antigen.

3. The method according to claim 2, wherein the adjuvanted modified recombinant SEQ ID NO: 4 is produced by a recombinant baculovirus.

4. The method according to claim 1, wherein the non-human mammal is a pig.

5. The method of claim 1, wherein the second species of mammal is human.

* * * * *